(12) United States Patent
Dinca et al.

(10) Patent No.: US 8,764,887 B2
(45) Date of Patent: Jul. 1, 2014

(54) METHODS FOR ELECTROCHEMICALLY INDUCED CATHODIC DEPOSITION OF CRYSTALLINE METAL-ORGANIC FRAMEWORKS

(75) Inventors: Mircea Dinca, Somerville, MA (US); Minyuan Li, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 135 days.

(21) Appl. No.: 13/439,355

(22) Filed: Apr. 4, 2012

(65) Prior Publication Data

US 2012/0297982 A1 Nov. 29, 2012

Related U.S. Application Data

(60) Provisional application No. 61/471,409, filed on Apr. 4, 2011.

(51) Int. Cl.
*B01D 53/22* (2006.01)

(52) U.S. Cl.
USPC ............... 96/4; 95/43; 95/45; 96/11; 96/12

(58) Field of Classification Search
USPC .................... 95/43, 45; 96/4, 11, 12
See application file for complete search history.

(56) References Cited

U.S. PATENT DOCUMENTS

| | | | | |
|---|---|---|---|---|
| 6,893,564 | B2 * | 5/2005 | Mueller et al. | 210/502.1 |
| 7,215,473 | B2 * | 5/2007 | Fleming | 359/585 |
| 7,662,746 | B2 * | 2/2010 | Yaghi et al. | 502/401 |
| 8,197,579 | B2 * | 6/2012 | Miller | 96/68 |
| 8,372,779 | B2 * | 2/2013 | Schubert et al. | 502/314 |
| 2009/0221418 | A1 * | 9/2009 | Fischer et al. | 502/155 |
| 2010/0322837 | A1 * | 12/2010 | Miller | 423/293 |
| 2011/0294658 | A1 * | 12/2011 | Lefevre et al. | 502/185 |
| 2012/0141685 | A1 * | 6/2012 | Gaab et al. | 427/373 |
| 2013/0204025 | A1 * | 8/2013 | Buso et al. | 556/130 |

FOREIGN PATENT DOCUMENTS

| | | |
|---|---|---|
| WO | WO-2007/131948 A2 | 11/2007 |
| WO | WO-2009/007267 A1 | 1/2009 |

OTHER PUBLICATIONS

Hermes et al. "Selective Nucleation and Growth of Metal-Organic Open Framework Thin Films on Patterned COOH/CF3-Terminated Self-Assembled Monolayers on Au(111)" (2005) Journal of American Chemical Society, 127, 13744-13745.*
Li et al., Reductive electrosynthesis of Crystalline Metal-Organic frameworks, J. Am. Chem. Soc., 133: 12926-12929 (2011).
International Search Report of PCT/US2012/032158, dated Oct. 12, 2012, 4 pages.
Written Opinion of PCT/US2012/032158, dated Oct. 12, 2012, 7 pages.

* cited by examiner

*Primary Examiner* — Jason M Greene
*Assistant Examiner* — Anthony Shumate
(74) *Attorney, Agent, or Firm* — Choate, Hall & Stewart LLP

(57) ABSTRACT

Embodiments of the invention relate to a method for preparing crystalline metal-organic frameworks (MOFs). The method includes the steps of providing an electrolyte solution in contact with a conductive surface, and applying a current or potential to the conductive surface in contact with the electrolyte solution. The electrolyte solution includes a protonated organic ligand, a metal ion, and a probase. Application of the reductive current or potential to the conductive surface produces the crystalline metal-organic framework (MOF) deposited on the conductive surface. The MOFs produced by the method may be incorporated into a gas separation membrane, a purification filter, and/or a sensor.

17 Claims, 14 Drawing Sheets

METHODS FOR ELECTROCHEMICALLY INDUCED CATHODIC DEPOSITION OF CRYSTALLINE METAL-ORGANIC FRAMEWORKS

CROSS-REFERENCE TO RELATED APPLICATION

This application claims priority to and the benefit of, and incorporates herein by reference in its entirety, U.S. Provisional Patent Application No. 61/471,409, which was filed on Apr. 4, 2011.

FIELD OF THE INVENTION

This invention relates generally to methods for preparing metal-organic frameworks (MOFs). More particularly, in certain embodiments, the invention relates to electrochemical methods for synthesis, surface deposition, and growth of crystalline metal-organic frameworks.

BACKGROUND OF THE INVENTION

Metal-organic frameworks (MOFs) are crystalline microporous materials with very high surface areas and ordered regular monodisperse pores. MOF pores generally range from about 0.25 nm to about 2.5 nm in diameter and are within the micropore and small mesopore regime. Because of their high porosity, MOFs have utility as materials for gas storage, gas separation, drug transport, molecular separations, catalysis, and sensors. However, current methods for producing MOFs are largely incompatible with many of the proposed applications. This is because many applications for MOFs, such as membranes for gas separation, require the MOF to be deposited or grown as continuous and crack-free films or membranes, hence the MOF material must be directly crystallized on a surface. Yet MOFs are solid, insoluble materials that are difficult to process, and it has been very challenging to grow MOFs on surfaces to date.

One method of growing MOF thin films/membranes is secondary growth crystallization. Initially, a first layer of seed nanocrystals is deposited on a macroporous support (e.g., $Al_2O_3$), and subsequently the seed layer is used to grow a continuous layer under solvothermal conditions. In some cases, better attachment is observed by prior functionalization of the macroporous support. This method requires multiple steps, and requires reaction under solvothermal conditions.

A second method is the Langmuir-Blodgett layer-by-layer approach, which relies on a Langmuir-Blodgett apparatus to make two dimensional MOF sheets, which can be then bridged by pyridine-based linkers between the sheets to form a three dimensional structure. Since the construction of the three dimensional structure relies on rinsing and immersing in a pyridine solution, and the metal clusters have open coordination for sheet linker ligands, this approach is not general in scope.

A third method of growing MOFs is in-situ crystallization. Here, a crystalline layer of a given MOF is grown directly on the bare surface of the support (or on a chemically modified support) in a one-step, one pot solvothermal synthetic procedure. The method requires heating the reaction mixture to provide solvothermal conditions.

A fourth method of preparing MOFs is gel-layer synthesis. Here, MOF materials are crystallized within a viscous gel layer and then transformed into films. As with in-situ crystallization, the gel-layer synthesis method requires heating the reaction mixture to provide solvothermal conditions.

A fifth method of preparing MOFs is referred to as liquid-phase epitaxial growth. This method requires sequential dipping of a functionalized surface in a solution containing either ligand or metal precursor. The solution usually does not contain both ligand and metal precursor at the same time. It is similar to epitaxial methods. The method is inefficient because solvent wash between dipping steps is often necessary and excess solution is needed to ensure enough component will remain to react with the next dipping step. For some MOFs, the approach is time-consuming because crystal growth may be slow.

A sixth method of preparing MOFs is anodic electrodeposition. This method has been used for the deposition of $Cu_3(BTC)_2$ (also known as HKUST-1, BTC=1,3,5-benzenetricarboxylate). It involves the oxidation of Cu metal electrodes to provide $Cu^{2+}$ ions, which react with $H_3BTC$ ligands in the electrolyte solution. Crystals of $Cu_3(BTC)_2$ are deposited on the Cu electrode. This method is limited because the deposition surface is continually being corroded to supply one of the main starting materials in the MOF synthesis. In addition, the metal contained in the MOF is limited to the type of metal electrode used as the anode (e.g., a Cu electrode can only give rise to Cu-based MOFs).

There is a need for improved methods of preparing MOFs that do not require multiple steps, that do not require maintaining solvothermal conditions, that do not require corrosion of the deposition surface to provide a material in the MOF synthesis, and that are not limited to only certain metal ions.

SUMMARY OF THE INVENTION

The invention relates to methods and systems for producing crystalline metal-organic frameworks (MOFs) that solve the problems above by electrochemically generating a Lewis basic species at a cathode surface. The basic species generated at the cathode deprotonate precursor ligands in an electrolyte solution, which then react with metal cations to form crystalline particles on the cathode and grow MOFs.

Electrochemically-induced cathodic deposition (also referred to herein as cathodic electrodeposition) of MOFs may be performed in a single step at room temperature—there is no need to maintain solvothermal conditions or perform multiple steps. Furthermore, unlike the anodic electrodeposition method discussed above, it is possible to use any of a wide variety of conductive surfaces and deposit MOFs composed of almost any metal ions and organic ligands thereon. The deposition surface need not provide a material for the MOF deposited thereon. Embodiments described herein allow crystallization in a single step with fast reaction times, wherein the reaction may be controlled, for example, by varying the current density and/or potential at the electroactive surface. Unlike the anodic electrodeposition method, the electroactive surface is not affected—it delivers electrons reductively and is not oxidized to deliver the metal ion that reacts to form the MOF. Any conductive surface can be used as the active cathode in embodiments described herein, and the methods are applicable to any metal ion in solution.

Because the cathode surface and no species in the active electrode are necessary to make up the MOF material, electrodes that are transparent can be used (e.g., fluorine doped tin oxide (FTO) and indium tin oxide (ITO)), which is particularly advantageous for applications in sensor technology, for example.

In one aspect, the invention relates to a method for preparing a crystalline metal-organic framework (MOF). The method includes the steps of providing an electrolyte solution in contact with a conductive surface, and applying a current or potential to the conductive surface in contact with the electrolyte solution, thereby producing the crystalline metal-organic framework (MOF) deposited on the conductive surface. The electrolyte solution includes a protonated organic ligand, a metal ion, and a probase.

In certain embodiments, the protonated organic ligand contains a proton with an acidity constant ($pK_a$ in water and at 25° C.) having a value from 0 to 15 such that the proton can be removed in situ by an electrochemically produced base species (e.g., a hydroxide anion or an amine). The organic ligand may include, for example, a carboxylic acid, a tetrazole, a 1,2,3-triazole, a 1,2,4-triazole, a pyrazole, a sulfonic acid, a phosphonic acid, a sulfinic acid, a phosphinic acid, and/or an imidazole. The metal ion may include, for example, $Zn^{2+}$, $Cu^{2+}$, $Co^{+2}$, $Co^{3+}$, $Ni^{2+}$, $Mn^{2+}$, $Mn^{3+}$, $Mn^{4+}$, $Fe^{2+}$, $Fe^{3+}$, $V^{2+}$, $V^{3+}$, $Cr^{2+}$, $Mo^{2+}$, $W^{2+}$, $Ru^{2+}$, $Os^{2+}$, $Cd^{2+}$, $Be^{2+}$, $Mg^{2+}$, $Ca^{2+}$, $Ba^{2+}$, $Sr^{2+}$, and/or, $Ln^{3+}$ where Ln is any of the lanthanide ions.

In various embodiments, the conductive surface includes fluorine doped tin oxide (FTO), indium tin oxide (ITO), silicon, carbon, graphite, zinc, cobalt, nickel, copper, titanium, iron, and/or steel. The conductive surface may catalyze the reduction of the probase to generate a base species (e.g., a hydroxide anion or an amine). In one embodiment, the conductive surface is transparent or semi-transparent. In some embodiments, the deposition of the crystalline metal-organic framework on the conductive surface is cathodic electrodeposition rather than anodic electrodeposition, such that the conductive surface does not undergo corrosion during the deposition.

In certain embodiments, the current or potential is applied to the conductive surface in contact with the electrolyte solution such that the probase is reduced at or near the conductive surface, thereby generating a base species (e.g., a hydroxide anion or an amine), wherein the protonated organic ligand is deprotonated in situ by reaction with the base species and wherein the deprotonated organic ligand reacts with the metal ion, thereby producing the crystalline metal-organic framework deposited on the conductive surface. The probase may include, for example, an oxoanion (e.g., nitrate ($NO_3^-$), perchlorate ($ClO_4^-$), and/or sulfate ($SO_4^{2-}$)). In some embodiments, the probase includes water, molecular oxygen ($O_2$), triethylammonium (or other ammonium cation), benzoquinone, a benzoquinone derivative, or the protonated organic ligand itself. The deposition of the crystalline metal-organic framework on the conductive surface may be performed in a single step and/or at room temperature. In various embodiments, a gas separation membrane, a purification filter, and/or a luminescent sensor include the crystalline metal-organic framework prepared by the method.

In one embodiment, a sensing device includes the crystalline metal-organic framework (MOF) prepared by the method. The conductive surface of the sensing device includes silicon and/or a transparent conductive material (e.g., FTO or ITO), and the MOF and the conductive surface are integrated into an electronic circuit.

In another aspect, the invention relates to a luminescent small molecule sensor. The sensor includes a crystalline metal-organic framework deposited on a transparent or semi-transparent substrate using the method. The metal-organic framework is intercalated with luminescent guest molecules that interact with the metal-organic framework in the presence of a specific small molecule, thereby producing a detectable (e.g., quantifiable) luminescence that is characteristic of the presence of the specific small molecule.

In another aspect, the invention relates to a crystalline metal-organic framework deposited on a transparent or semi-transparent substrate using the method.

In another aspect, the invention relates to a sensing device. The sensing device includes a crystalline metal-organic framework (MOF) deposited on a conductive surface using the method. The surface includes silicon and/or a transparent conductive material (e.g., FTO or ITO). The MOF and the conductive surface are integrated into an electronic circuit.

Elements of embodiments described with respect to a given aspect of the invention may be used in various embodiments of another aspect of the invention. For example, it is contemplated that features of dependent claims depending from one independent claim can be used in apparatus and/or methods of any of the other independent claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

DETAILED DESCRIPTION OF ILLUSTRATIVE EMBODIMENTS

Figure 1:
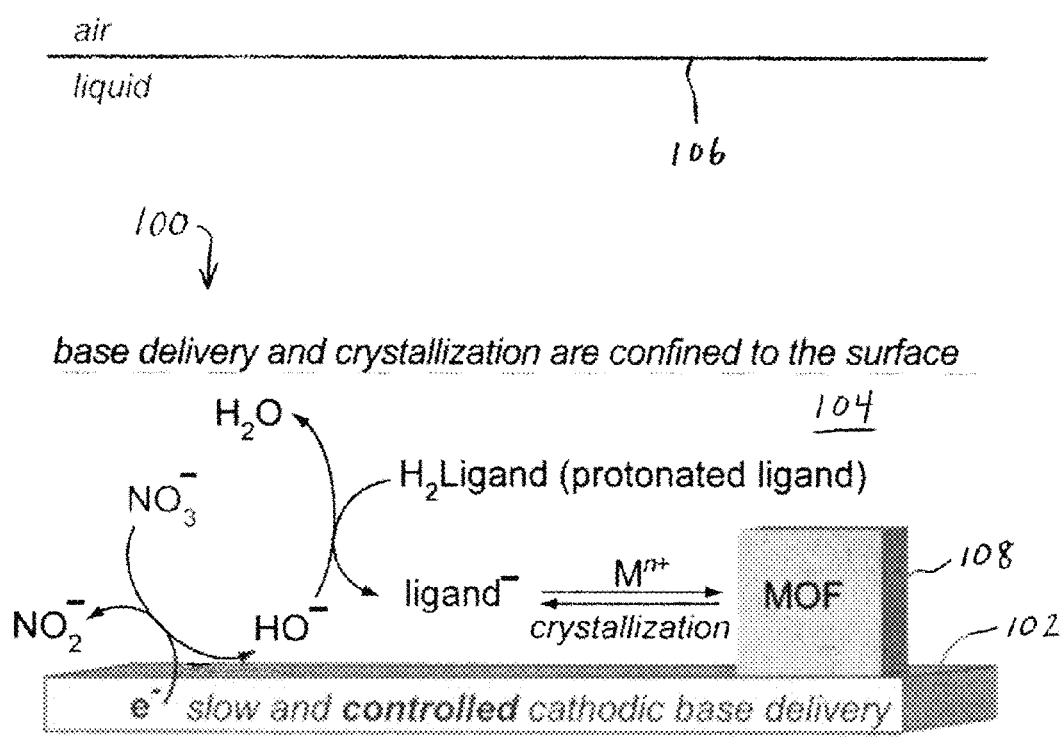
FIG. 1 is a schematic drawing of a method for the cathodic electrochemically-induced deposition of crystalline MOF compounds, according to an illustrative embodiment of the invention.

Throughout the description, where solutions or compositions are described as having, including, or comprising specific components, or where processes and methods are described as having, including, or comprising specific steps, it is contemplated that, additionally, there are solutions and compositions that consist essentially of, or consist of, the recited components, and that there are processes and methods that consist essentially of, or consist of, the recited processing steps, within the scope of embodiments discussed herein.

It should be understood that the order of steps or order for performing certain actions is immaterial so long as the invention remains operable. Moreover, two or more steps or actions may be conducted simultaneously.

It is contemplated that methods, systems, and processes of the claimed invention encompass scale-ups, variations, and adaptations developed using information from the embodiments described herein. For example, the invention includes pilot plant and plant-scale manufacturing processes whose feasibility is demonstrated by the laboratory-scale experiments described herein. The electrochemical reactions described herein may be performed using reactor equipment that is known to those of ordinary skill in the art. Reactions described herein may be conducted in batch, semi-continuous, and/or continuous operation.

Scale-up of systems from laboratory to plant scale may be performed by those of ordinary skill in the art. For example, those of ordinary skill in the art may select electrochemical reactor types, design experiments for obtaining kinetic data, develop and apply models for reactor design, develop economically optimum reactor design, and/or validate reactor designs via pilot plant and/or full scale electrochemical reactor experiments.

Embodiments of the invention may be performed as part of a continuous, semi-continuous, or batch process. Reactors may be single-stage or multi-stage. It is contemplated that methods of the invention may be combined or supplemented with reactors, systems, or processes that are known in the art.

As used herein, the term "probase" can refer to either a charged or neutral species. Similarly, as used herein, the term "base species" can refer to either a charged or neutral species. Likewise, as used herein, the term "molecule" can refer to either a charged or neutral species.

The mention herein of any publication, for example, in the Background section, is not an admission that the publication serves as prior art with respect to any of the claims presented herein. The Background section is presented for purposes of clarity and is not meant as a description of prior art with respect to any claim.

Described herein are methods for growth and synthesis of MOFs that result in direct deposition of MOF crystals and crystalline films on a conductive surface. The approach involves electrochemical generation of base species (such as hydroxide, $OH^-$, or amine) by reduction of a probase (e.g., water, an oxoanion such as $NO_3^-$, $ClO_4^-$, or $SO_4^{2-}$, molecular oxygen, triethylammonium or other ammonium cations, benzoquinone or benzoquinone derivatives, or any redox active molecules with proton-coupled electron transfer) at a conductive surface (e.g., an electrode). The base species, such as hydroxide anions or amines, generated at the cathode deprotonate precursor ligands in the electrolyte solution, which then react with metal cations to form crystallite particles on the conductive surface. The method affords the crystallization of MOF materials directly on the conducting surface because the entire electrochemical/synthetic process may be confined to the immediate proximity of the electrode surface. In certain embodiments, this immediate proximity is a thickness of up to about 1 mm from the electrode surface, although it should be noted that film thickness can be controlled by time of deposition and the applied potential/electric field. In certain applications, such as in gas separation, the thickness may be 100 micrometers or less.

Methods of cathodic electrochemically-induced deposition of crystalline MOF compounds described herein involve: 1) electrochemical cathodic base generation (e.g., cathodic generation of hydroxide ion and/or other basic species); 2) ligand deprotonation by the generated basic species; and 3) MOF crystallization via reaction of the anionic ligands with metal ions near the electrode. For example, FIG. 1 illustrates a mechanism 100 for electrochemically induced cathodic deposition of crystalline MOF compounds, in accordance with certain embodiments of the invention. A conductive surface 102 is exposed to or immersed within an electrolyte solution 104, below a liquid-air interface 106. The electrolyte solution 104 contains protonated organic ligands, metal ions (Mn, a nitrate ($NO_3^-$) probase, and water ($H_2O$). An electrical current or potential is applied to the conductive surface 102 where the nitrate is reduced to produce hydroxide ($OH^-$) anions. The hydroxide anions in turn deprotonate the organic ligands, which react with the metal ions ($M^{n+}$) to produce crystals of MOF material 108, deposited on the conductive surface 102.

Figure 2:
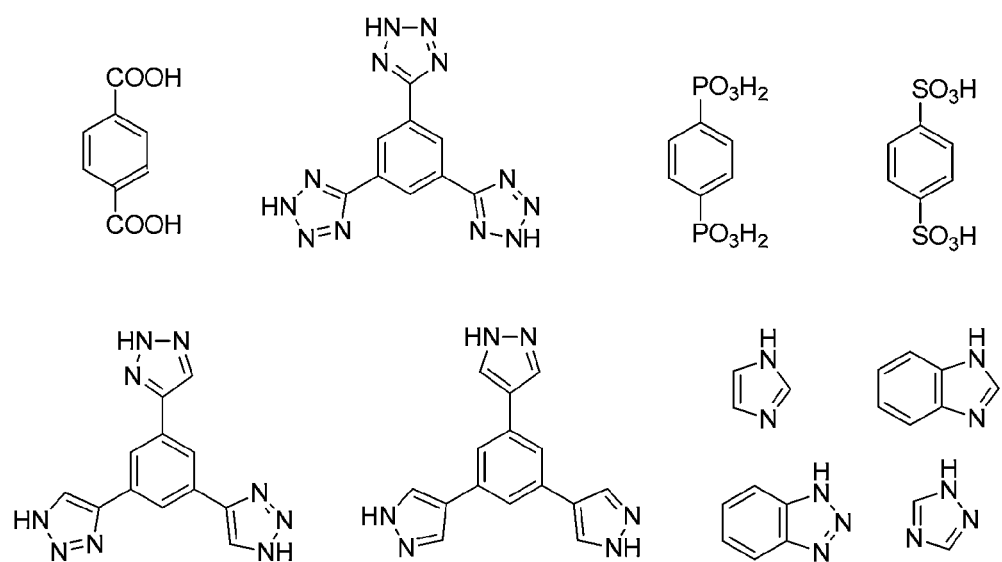
FIG. 2 depicts organic ligands used in electrochemically induced cathodic deposition of crystalline MOF compounds, according to an illustrative embodiment of the invention.

In some embodiments, the organic ligand contains a proton with an acidity constant ($pK_a$ in water and at 25° C.) ranging between 0 and 15, such that this proton can be removed (and ligand deprotonated) by the electrochemically produced base species (e.g., $OH^-$) in situ. Ligand classes that fall in this category include but are not limited to: carboxylic acids; tetrazoles; 1,2,3-triazoles; 1,2,4-triazoles; pyrazoles; sulfonic acids; phosphonic acids; sulfinic acids; phosphinic acids; phenols; imidazoles, and mixed O-, N-, and/or S-containing heterocycles that have one heteroatom-bound proton with pKa (in water and at 25° C.) in the range 0-15. FIG. 2 depicts organic ligands for use in electrochemically induced cathodic deposition of crystalline MOF compounds, in accordance with various embodiments of the invention.

The functional groups may be installed on any type of organic linker (e.g., a benzene may be used as a ligand backbone, as shown in FIG. 2), but the ligands can have any number of atoms in any geometry. In various embodiments, the only requirement is that the ligand contains one or more acidic groups with a pKa (in water and at 25° C.) in the range 0 to 15.

The organic ligand (such as those listed above and/or shown in FIG. 2) may contain any number of acidic groups, and the groups can be combined in any combination. In various embodiments, the organic ligand includes at least one acidic group. For example, the electrolyte solution may contain a single organic ligand or multiple organic ligands. In the case of multiple organic ligands, new MOF materials may be deposited that contain all these organic ligands.

A non-limiting list of example metal ions that can be used in the embodiments described herein is as follows: $Zn^{2+}$, $Cu^{2+}$, $Cu^+$, $Co^{2+}$, $Co^{3+}$, $Ni^{2+}$, $Mn^{2+}$, $Mn^{3+}$, $Mn^{4+}$, $Fe^{2+}$, $Fe^{3+}$, $V^{2+}$, $V^{3+}$, $Cr^{2+}$, $Mo^{2+}$, $W^{2+}$, $Ru^{2+}$, $Os^{2+}$, $Cd^{2+}$, $Be^{2+}$, $Mg^{2+}$, $Ca^{2+}$, $Ba^{2+}$, $Sr^{2+}$, $Ln^{3+}$ (were Ln is any of the lanthanide ions), etc. In general, the metal ions could be either of the metals contained in the main group, transition group, lanthanide, or actinide metal series, in any oxidation state. The more common examples are listed above. Monovalent, divalent and trivalent transition metal ions are most prevalent (e.g., $Zn^{2+}$, $Cu^{2+}$, $Cu^+$, $Co^{2+}$, $Co^{3+}$, $Ni^{2+}$, $Mn^{2+}$, $Fe^{2+}$, $Fe^{3+}$, $V^{2+}$, $V^{3+}$, $Cr^{2+}$, $Mo^{2+}$, $W^{2+}$, $Ag^+$, $Hg^{2+}$).

The illustrative example for cathodic electrochemically induced deposition of crystalline MOF compounds which follows involves the deposition of $Zn_4O(O_2C—C_6H_4—CO_2)_3$ (MOF-5), an iconic MOF material. As described below, because of the experimental concept and design, this method may be applied for any MOF material. The method is generally independent of the nature of the organic ligand or metal ion precursor.

Ligand deprotonation preferably occurs in-situ by reaction with the base species generated at the cathode. Hydroxide anion (base) is generated by reduction of water or oxoanions according to, but not limited to reactions such as those in Table 2. The potentials shown in the table are thermodynamic values.

TABLE 2

Examples of hydroxide producing electrochemical reactions.

| Reaction | E°(V) |
|---|---|
| $NO_3^- + 2H^+ + 2e^- \rightarrow NO_2^- + H_2O$ | 0.93 V |
| $NO_3^- + 10H^+ + 8e^- \rightarrow NH_4^+ + 3H_2O$ | 0.81 V |
| $ClO_4^- + 4H_2O + 8e^- \rightarrow Cl^- + 8HO^-$ | 0.51 V |
| $ClO_4^- + H_2O + 2e^- \rightarrow ClO_3^- + 2HO^-$ | 0.36 V |
| $NO_3^- + 7H_2O + 8e^- \rightarrow NH_4^+ + 10HO^-$ | 0.15 V |
| $NO_3^- + 2H_2O + 2e^- \rightarrow NO_2^- + 2HO^-$ | 0.01 V |
| $2H_2O + 2e^- \rightarrow H_2 + 2HO^-$ | −0.83 V |

In certain embodiments, probase (e.g., water and/or oxoanion) reduction for hydroxide generation is controlled by applying a constant potential in the range 0 to −5 V vs. NHE (Normal Hydrogen Electrode) and/or by applying a constant current. Water or oxoanion reduction occurs generally at a conductive or electroactive surface (e.g., Indium Tin Oxide (ITO), FTO, carbon/graphite, zinc, cobalt, nickel, copper, or other metallic surfaces). The base generation electroreduction may be catalyzed by the electroactive surface (e.g., nitrate, $NO_3^-$, anion reduction is catalyzed by Cu or Zn surface).

In various embodiments, the probase is a stable molecule or ion in solution that may be electrochemically reduced to form the active base species for deprotonation of the ligand. In general, any molecular species that becomes a proton acceptor upon reduction may serve as a suitable probase for the methods and processes described herein. For example, in the electrodeposition of MOF-5, nitrate may serve as a probase for generating the base species necessary for ligand (e.g., $H_2BDC$) deprotonation. Additional suitable probases include, for example, triethylammonium (e.g., reduction of triethylammonium produces triethylamine) molecular oxygen (e.g., $O_2$ reduction in the presence of water produces hydroxide), and benzoquinone. Even when the probase exhibits reversible protonation, the cathodic potential at the electrode may allow a fraction of free ligands to exist. In some embodiments, the protonated ligands themselves function as probases (e.g., reduction of $H_2BDC$ with evolution of $H_2$ generates $HBDC^-$, which can itself participate in the deposition process).

Hydroxide (or other base) generated at the electrode reacts with protonated ligand (e.g., $H_2BDC$ (1,4-benzenedicarboxylate)) to provide deprotonated ligand, which then reacts with metal ion species (e.g., $Zn^{2+}$) to form crystals of MOF material (e.g., MOF-5). Advantageously, deposition of MOF materials under these conditions does not require thermal decomposition of formamide-based solvents, and hence solvothermal conditions are not required. Deposition of MOF materials under these conditions may occur in shorter periods than normally required with solvothermal conditions. For example, MOF deposition rates may range from several nanometers per minute to about 2 micrometers per minute. In certain embodiments, the deposition rate can exceed 2 micrometers per minute. In one embodiment, the deposition rate is about 1.3 micrometers per minute. Deposition rates are generally dependent on process parameters, such as temperature, reactant concentrations, and the current density or voltage at the conductive surface.

The methods and processes described herein may be performed under a wide range of process conditions. For example, process temperatures may be from about 0° C. to about 100° C. In one embodiment, the process temperature is about 25° C., or about room temperature. As mentioned, solvothermal conditions are not required. Likewise, the process pressures may be from about 0.5 atm up to about 10 atm. The process pressure is preferably about one atmosphere.

In various embodiments, the electrolyte solution in contact with the conductive surface includes a protonated organic ligand, a metal ion, and a probase (e.g., water and/or an oxoanion). The concentration of protonated organic ligand in the electrolyte solution may be, for example, from about 10 mM to about 100 mM. In one embodiment, the protonated organic ligand concentration is about 50 mM. Likewise, the concentration of metal ion in the electrolyte may be, for example, from about 10 mM to about 200 mM. For example, the metal ion concentration may be about 150 mM. The concentration of probase may be, for example, from about 3 mM to about 300 mM. The probase concentration is preferably about 150 mM. pH values for the electrolyte solution are generally from about 3 to about 11 for aqueous solutions, or equivalent scales in other solvents. For example, the pH may be about 7.

In general, to perform the cathodic electrodeposition methods described herein, an electrical current or electrical potential is applied or delivered to the conductive surface. The electrical current may be applied to achieve current densities, for example, from about 0.1 mA/cm² to about 100 mA/cm². In one embodiment, the current density is about 3 mA/cm². Likewise, voltages applied to the conductive surface may be, for example, from about −0.1 V to about −100 V. In some embodiments, the voltages are about −1.5 V.

The methods and processes described herein are suitable or compatible with a wide-variety of chemical manufacturing processes, including batch processes, semi-batch processes, or continuous processes. In certain embodiments, reaction ingredients (e.g., the metal ions and the probase) are fed (e.g., continuously) into a reactor, and process conditions (e.g., temperatures, pressures, concentrations, etc.) are monitored and controlled.

In various embodiments, the conductive surface used for the cathodic electrodeposition may have any shape. For example, the shape of the conductive surface may be circular, tubular, cylindrical, flat, spherical, rectangular, triangular, conical, or pyramidal. In general, the shape of the conductive surface defines the shape of the deposited MOF film.

Compared to previous methods for producing MOFs, the methods and processes described herein provide several advantages. For example, MOF film deposition is conformal to the electrode surface, which is not obtainable via a processing technique such as spin-coating. The films are also free of defects and cracks during the synthesis, since any cracks exposing the substrate will be active for electrochemical crystal growth from the electrode up. Further, cathodic electrodeposition allows for use of a conductive surface or substrate that is independent of the MOF being grown. This is in contrast with anodic electrodeposition, for example, which relies on corroding the underlying metal electrode to supply the metal ions necessary for MOF formation. Embodiments of the methods described herein do not corrode the conductive substrate.

The methods described herein are also faster than previous methods, and they may be performed at room temperature. For example, cathodic electrodeposition of MOF-5 is observed on FTO after less than 15 minutes. This indicates the method is viable for larger scale production with higher synthetic turnovers. Advantageously, metal formation on the conductive surface (e.g., metallic zinc formation on FTO) may provide anchoring to MOF crystallites, which by themselves may not have strong interactions with the substrate. Another advantage of these methods is that they allow the deposition process to be controlled with different applied electrical potential steps or values. This provides access to different probases and thus different phases within one pot of starting reagents.

The methods described herein also allow the production of MOFs that have not yet been produced or obtained using previous methods (e.g., traditional solvothermal methods). For example, the new methods are capable of utilizing metal ions that have not yet been utilized with previous anodic deposition methods. As discussed below in the Examples, one such material utilizes $Mn^{2+}$ instead of $Zn^{2+}$.

The MOFs produced using the methods and processes described herein have many different applications, across a wide variety of industries. For example, the MOFs may be used for the heterogeneous separation of gases and liquids. In general, MOFs are promising materials for separating gases from various mixtures. Examples include the separation of $CH_4$ from $CO_2$; $N_2$ from $H_2$; $O_2$ from $N_2$; alkanes from alkenes; meta- from para- from ortho-xylenes; CO from $H_2$, $H_2S$ from $CH_4$, $O_2$ from $H_2$, and others. Separations generally require MOFs to be incorporated into membranes. Advantageously, the current method may be used to grow membranes of MOFs on conductive substrates (e.g., macroporous steel or aluminum tubes), thereby providing utility in gas separation devices.

The MOFs produced using the methods described herein also have applications in filtration devices. For example, the MOFs may be used as filters for purification processes, such as the removal of toxins from cigarette smoke in small volume AC systems (e.g., in cars and other small closed spaces).

In various embodiments, the MOFs produced using the methods described herein are used in sensing devices, such as small molecule luminescent sensors. The permanent porosity of MOFs generally allows intercalation of guest molecules. When guest molecules interact with an MOF, a response can be read when a signal transduction mechanism is present. Detection of luminescence is one such signal, and it often requires the deposition of the sensing substrate as thin films on transparent surfaces. Advantageously, the methods described herein may be used for the deposition of MOFs on any transparent conducting surface (e.g., FTO and ITO) and may therefore be used for the fabrication of luminescent sensing devices. In some embodiments, the observed luminescent signal arises from changing the metal-center coordination environment, exciplex formation, and/or radiation-induced ionization.

These MOFs may also be used to produce sensing devices based on electrical signal transduction. Such devices generally require interfacing a sensing substrate with a conductive surface, in an electronic circuit. Advantageously, the cathodic deposition of MOFs on substrates such as silicon or transparent conductive electrodes provides great versatility for device integration. The methods described herein may provide fast and robust interfacing of MOFs with a variety of conductive substrates.

EXPERIMENTAL EXAMPLES

Example 1

A working electrolyte solution was produced by dissolving tetrabutylammonium hexafluorophosphate ($TBAPF_6$, 1.94 g, 5.01 mmol, Sigma-Aldrich, 99.0% purity) in 50 mL of N,N-dimethylformamide (DMF) in a 100 mL Airfree® storage vessel. DMF was previously dried and deaerated through a solvent purification column. A quantity of 0.5 mL of water (Ricca, ASTM Type I, 18 MΩ cm resistivity) was subsequently added to the DMF solution to provide a 1% water content. Water is necessary for cathodic generation of hydroxide (see Table 1). The working electrolyte solution was deaerated once again using three consecutive freeze-pump-thaw cycles. The vessel was then brought into a nitrogen-filled glovebox. All further electrochemical experiments were performed inside the glovebox to avoid $O_2$ contamination of the solution. $O_2$ can get reduced itself, thus interfering with cathodic processes due to reduction. However, in an industrial setting, this step may not be necessary, because the reactor may be designed to eliminate the need for an $N_2$ atmosphere.

For the electrochemistry experiments, 20 mL of the working electrolyte solution was added to each side of a custom two-component H-type electrochemical cell. The anode and cathode compartments are separated by a fitted glass disk to avoid cross-contamination of the analytes produced at the working (cathode) and counter (anode) electrodes. Terephthalic acid (150 mg, 0.90 mmol, Sigma-Aldrich, 98%) and 150 mg of zinc nitrate hydrate (0.62 mmol, Strem, 98%) were added to one compartment of the H-Cell, and stirred until complete dissolution.

Figure 3A:
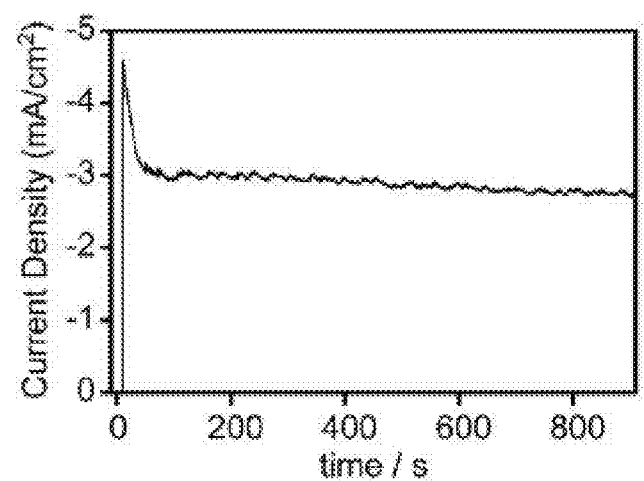
FIGS. 3a and 3b include graphs depicting electrochemical deposition traces using FTO electrodes, 0.1 M $TBAPF_6$ electrolyte in dimethylformamide (DMF) (with 1% watery, with a concentration of 45 mM $H_2BDC$ and 31 mM $Zn^{2+}$, at constant potential (−1.6V vs. Ag/Ag (crypt)) (FIG. 3a), and a current density of 1.6 mA/cm$^2$ (FIG. 3b), according to an illustrative embodiment of the invention.
Figure 3B:
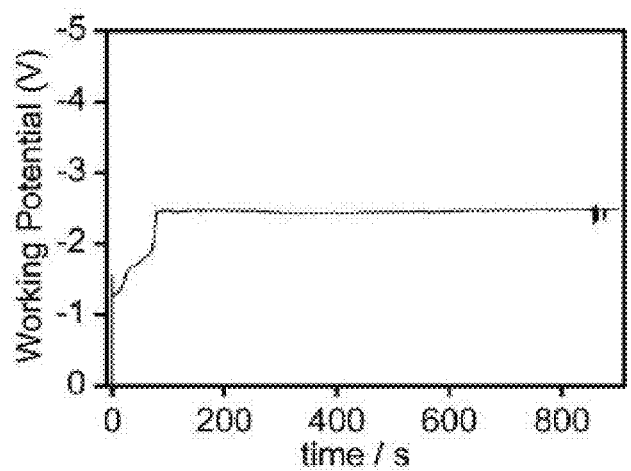

In the above experiment, the working electrode was a fluorine-doped tin oxide (FTO)-coated glass plate (L×W×H=10× 25×3 mm) suspended by a small Cu alligator clip and copper wire above the cell. The electrode surface in contact with the solution was approximated at 1 $cm^2$. FTO plates were cleaned with distilled water and acetone prior to usage. The auxiliary electrode consists of a piece platinum gauze (1 $cm^2$, 100 mesh, 99.9% trace metal basis) attached to a platinum wire auxiliary electrode (BASi). A silver-silver cryptand electrode immersed in a solution of 0.1 M TBAPF$_6$ in DMF inside a glass rod fitted with a Vycor tip served as the reference electrode. To construct the silver-silver cryptand (Ag/AgCrypt) reference electrode, AgNO$_3$ (16.9 mg, 0.100 mmol) and [2.2.2]cryptand (Kryptofix® 222, 155 mg, 0.412 mmol) (E°$_{Ag/Ag\,(crypt)}$=0.527 V vs. Fc/Fc$^+$). A nonaqueous reference electrode kit (BASi) was used to construct the Ag/AgCrypt reference electrode. Electrochemically induced synthesis of MOF-5 can be achieved either by applying a constant potential or a constant current to the working electrode. A BioLogic SP200 potentiostat/galvanostat was utilized for this purpose. Current/time and potential/time deposition traces are shown in FIG. 2. Scanning electron micrographs showing crystallites with well-defined faces and edges deposited by applying a constant potential of −1.6 V are shown in FIG. 3.

Figure 4A:
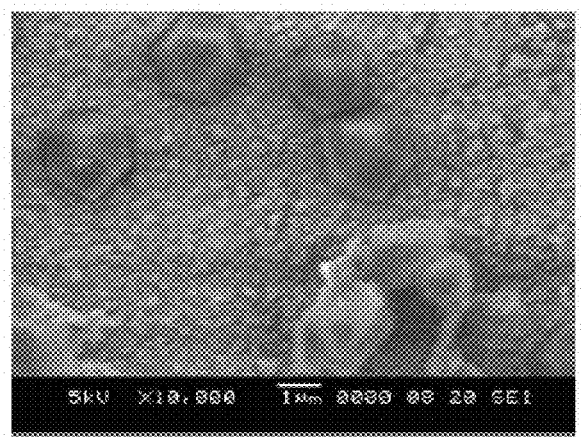
FIGS. 4a and 4b include scanning electron micrographs of the crystalline film of MOF-5 deposited at a constant potential of −1.6V vs. Ag/Ag (crypt), as described in FIGS. 3a and 3b, according to an illustrative embodiment of the invention.
Figure 4B:
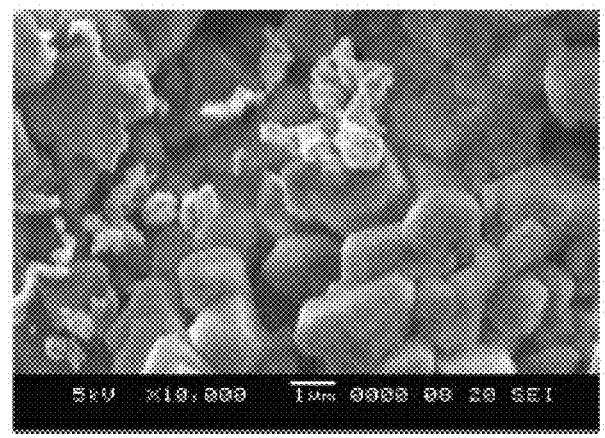
Figure 5A:
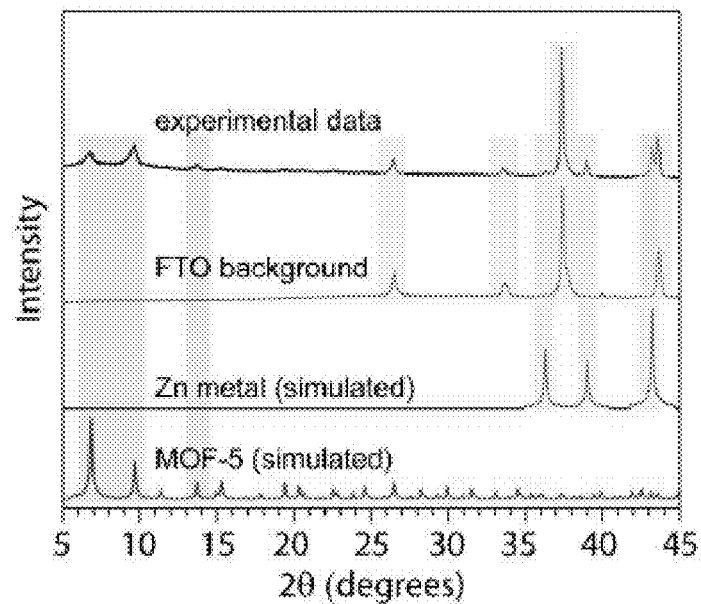
FIGS. 5a and 5b include graphs of powder X-ray diffraction data for the crystalline film deposited at constant potential (−1.6V) (FIG. 5a), and constant current (1.6 mA/cm$^2$) (FIG. 5b), as described in FIGS. 3a and 3b, according to an illustrative embodiment of the invention.
Figure 5B:
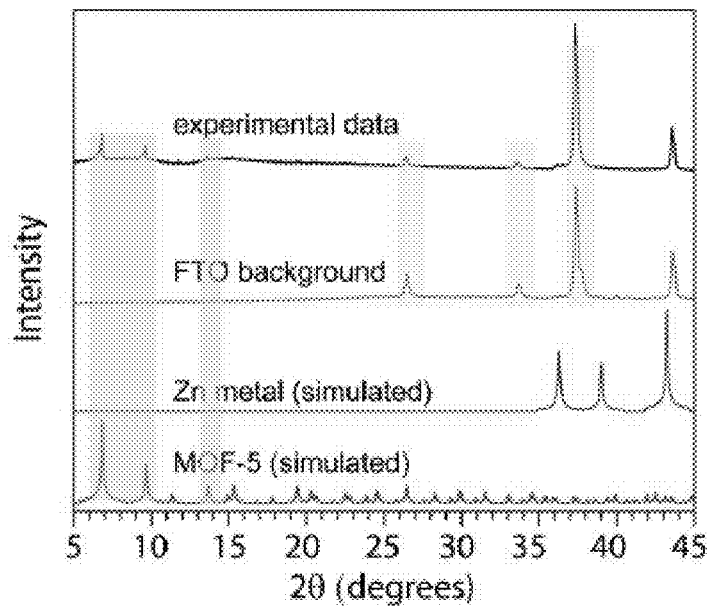

FIG. 4 shows powder X-ray diffraction patterns for similar MOF-5 films deposited under cathodic bias. The experimental data (top) shows that the only crystalline MOF phase deposited under cathodic potentiostatic or galvanostatic conditions is MOF-5. Thus, MOF-5 can be deposited in crystalline form with no other phase deposited under the conditions. In the second trace from the top of FIG. 4, it can be seen that Zn metal is also deposited. Thus, crystalline Zn metal peaks are apparent in some cases, indicating that Zn metal is deposited under these potentials (−1.0 to −2.5 V). Zn metal likely contributes to nitrate/water reduction catalysis, which is important for hydroxide generation.

The cathodic electrodeposition methods can be extended to the synthesis of isoreticular analogues of MOF-5 and other Zn—BDC coordination polymers, with different secondary building units. The cathodic electrodeposition approach may be used in a wide variety of reaction conditions.

Example 2

Figure 6:
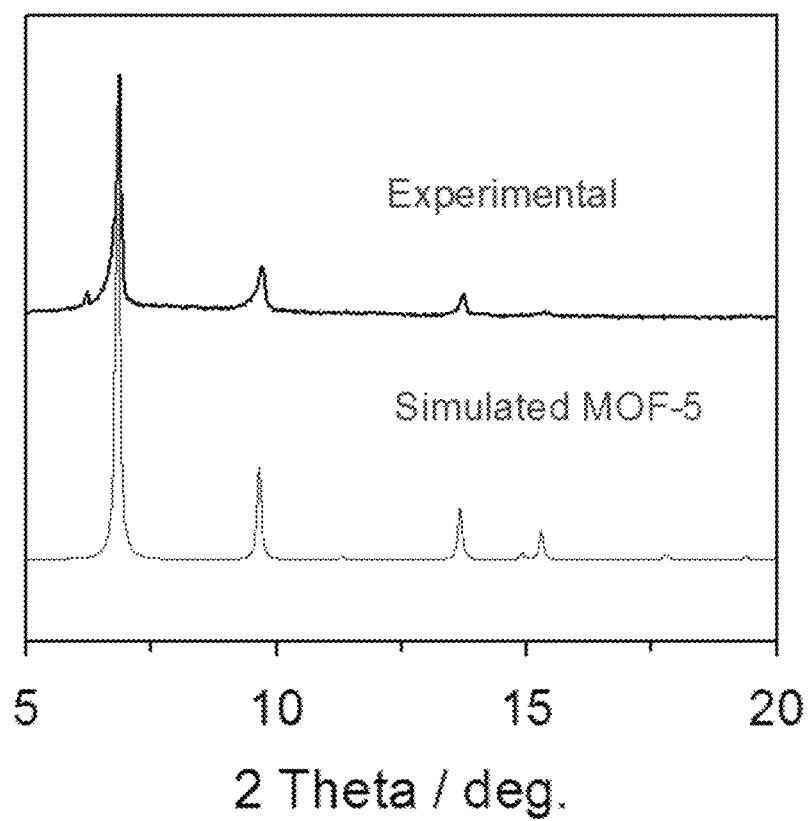
FIG. 6 is a graph of powder X-ray diffraction results for $Zn_4O(NH_2—BDC)_3$ (IRMOF-3) synthesized using cathodic electrodeposition, according to an illustrative embodiment of the invention.

Cathodic electrodeposition was used to synthesize Zn$_4$O(NH$_2$-BDC)$_3$ (IRMOF-3). The procedure began by dissolving 45 mg of NH$_2$-BDC (2-amino-1,4-benzenedicarboxylic acid) and 345 mg of Zn(NO$_3$)$_2$*4.5H$_2$O in a 10 mL solution of 0.1M TBAPF$_6$ (tetrabutylammoniumhexafluorophosphate) in DMF (N,N-dimethylformamide, dried and deaerated with argon) and 1% v/v water. The solution was shaken vigorously until dissolution and transferred to a two compartment glass H-cell equipped with a sintered glass filter. An FTO-covered glass working electrode was used, with a 1 cm$^2$ platinum mesh counter electrode, and a Ag/Ag (cryptand) reference electrode. Approximately 1×1 cm$^2$ of active electrode was exposed to solution. The cell was capped and purged with N$_2$ for 30 minutes, before electrolyzing at −1.5 V for 15 minutes under a N$_2$ blanket. Yellow-brown crystallites formed on the FTO surface along with metallic zinc. Referring to the X-ray diffraction results and predictions in FIG. 6, IRMOF-3 is isostructural with MOF-5. Qualitatively, based on the relative peak intensity in this figure, a fraction of the product generated is not interpenetrated.

Example 3

Figure 7:
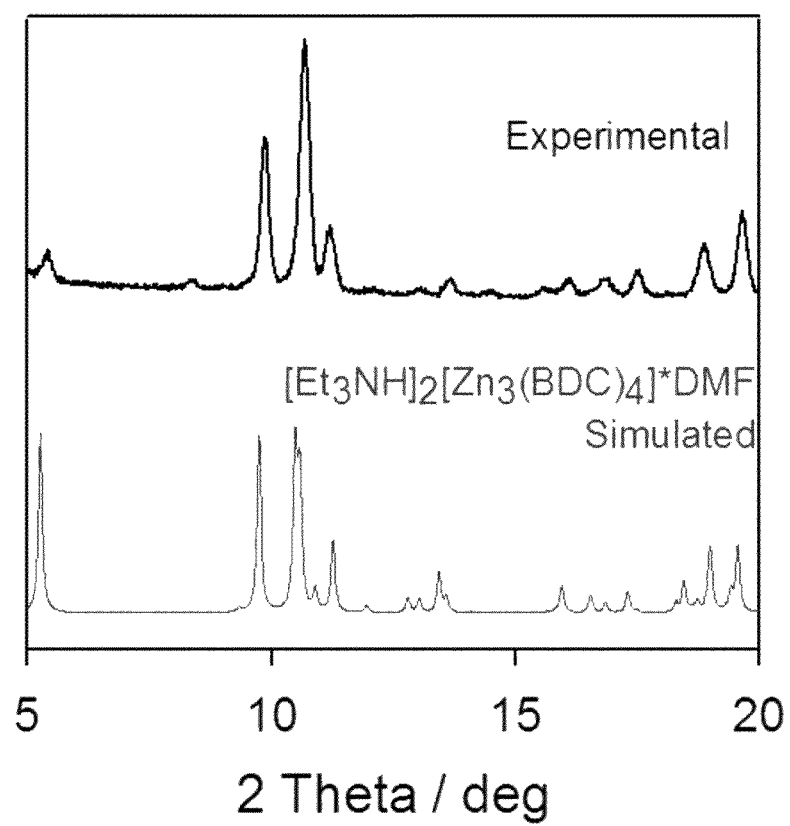
FIG. 7 is a graph of powder X-ray diffraction results for $[Et_3NH]_2[Zn_3(BDC)_4]$*DMF synthesized using cathodic electrodeposition, according to an illustrative embodiment of the invention.

Cathodic electrodeposition was used to synthesize [Et$_3$NH]$_2$[Zn$_3$(BDC)$_4$]*DMF. The process began by stirring 84 mg of H$_2$BDC, 500 mg of Zn(NO$_3$)$_2$*8H$_2$O, and 500 mg of Et$_3$NHCl (triethylammonium chloride) in a 10 mL solution of 0.1 M TBAPF$_6$ in dry and deaerated DMF solution. The stirring was performed under a nitrogen purge for 30 minutes inside a custom H-cell, containing a 1 cm$^2$ Pt mesh working electrode, a 4 cm$^2$ Pt mesh counter electrode, and a Ag/Ag (cryptand) reference electrode. A constant potential of −1.5 V was applied for 4 hrs. A gray solid layer was observed to form on the electrode after deposition. A small amount of Zn(BDC)*DMF was found to co-precipitate. X-ray diffraction results and predictions for the material produced during the experiment are presented in FIG. 7.

Example 4

Figure 8:
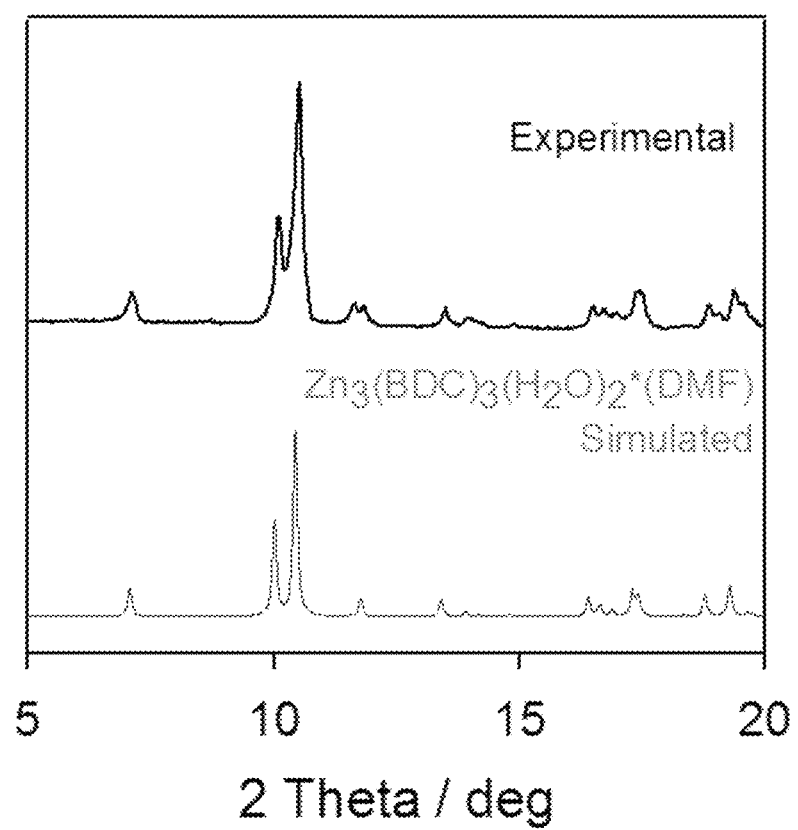
FIG. 8 is a graph of powder X-ray diffraction results for $Zn_3(BDC)_3(H_2O)_2$*DMF synthesized using cathodic electrodeposition, according to an illustrative embodiment of the invention.

Cathodic electrodeposition was used to synthesize Zn$_3$(BDC)$_3$(H$_2$O)$_2$*DMF. The process began by dissolving 84 mg of H$_2$BDC (1,4-benzenedicarboxylic acid) and 240 mg of Zn(NO$_3$)$_2$*6H$_2$O in a 10 mL solution of 0.1 M TBAP (tetrabutylammonium perchlorate) in DMF (obtained from solvent column system, dried and deaeriated with argon). The solution was transferred into a custom H-cell with a 1 cm$^2$ Pt mesh working electrode, a 4 cm$^2$ Pt mesh counter electrode, and a Ag/Ag (cryptand) reference electrode. The cell was then capped, stirred, and purged with 99.9% compressed oxygen at a pressure slightly above one atmosphere until complete dissolution of the solids occurred. The stirring was then stopped and the cell was put under an O$_2$ blanket. Electrolysis was performed at −1.00 V for 14 hours. A colorless layer of solid was observed to cover the entire active electrode. Upon drying in air, the colorless solid turned white. X-ray diffraction results and predictions for the material produced during the experiment are presented in FIG. 8.

Example 5

Zn$_3$(BDC)$_3$(H$_2$O)$_2$*DMF was synthesized by cathodic electrodeposition. Zn(BDC)(H$_2$O)*DMF co-precipitates with Zn(BDC)(H$_2$O). The synthesis and experimental results are presented below with the co-precipitate.

Figure 9:
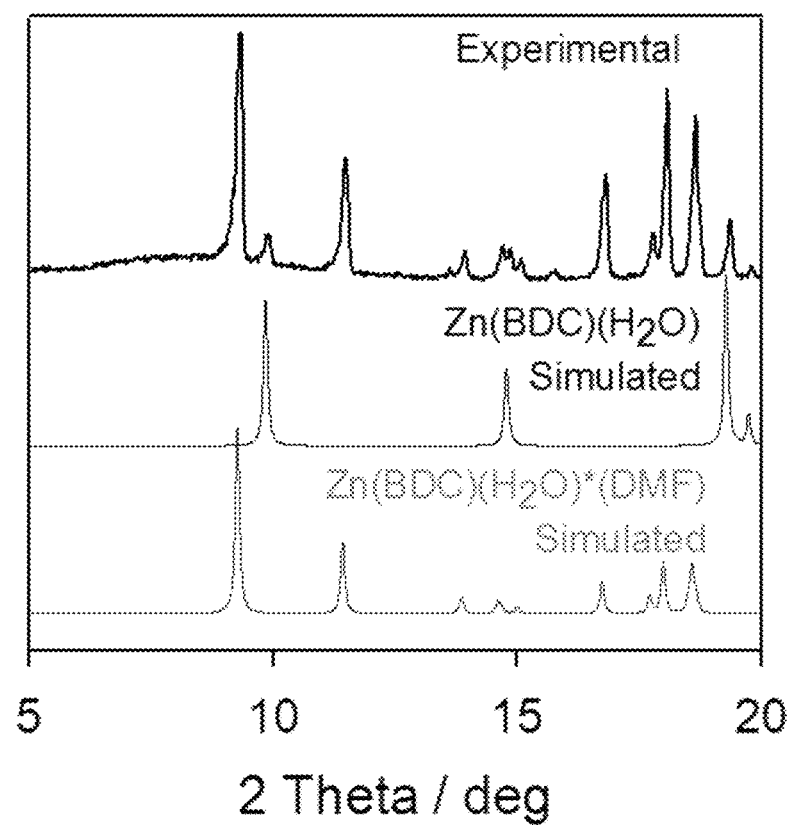
FIG. 9 is a graph of powder X-ray diffraction results for $Zn(BDC)(H_2O)$ and $Zn(BDC)(H_2O)$*(DMF) synthesized using cathodic electrodeposition, according to an illustrative embodiment of the invention.

Zn(BDC)(H$_2$O) was synthesized by dissolving 85 mg of H$_2$BDC and 400 mg of Zn(NO$_3$)$_2$*8H$_2$O in a 10 mL solution of 0.1 M TBAPF$_6$ in DMF (used as received). The solution was then transferred to a custom H-cell and purged with a gas stream of 10% O$_2$ in Ar. The cell contained a 1 cm$^2$ Pt mesh working electrode, 1 cm$^2$ Pt mesh counter electrode, and a Ag/Ag (crpytand) reference electrode. The cell was then electrolyzed at a potential of −0.7 V for 16 hours. A colorless layer of solid covered the entire active electrode. Upon drying in air, the colorless solid turned white. X-ray diffraction results and predictions for the material produced during the experiment are presented in FIG. 9.

Example 6

Figure 10:
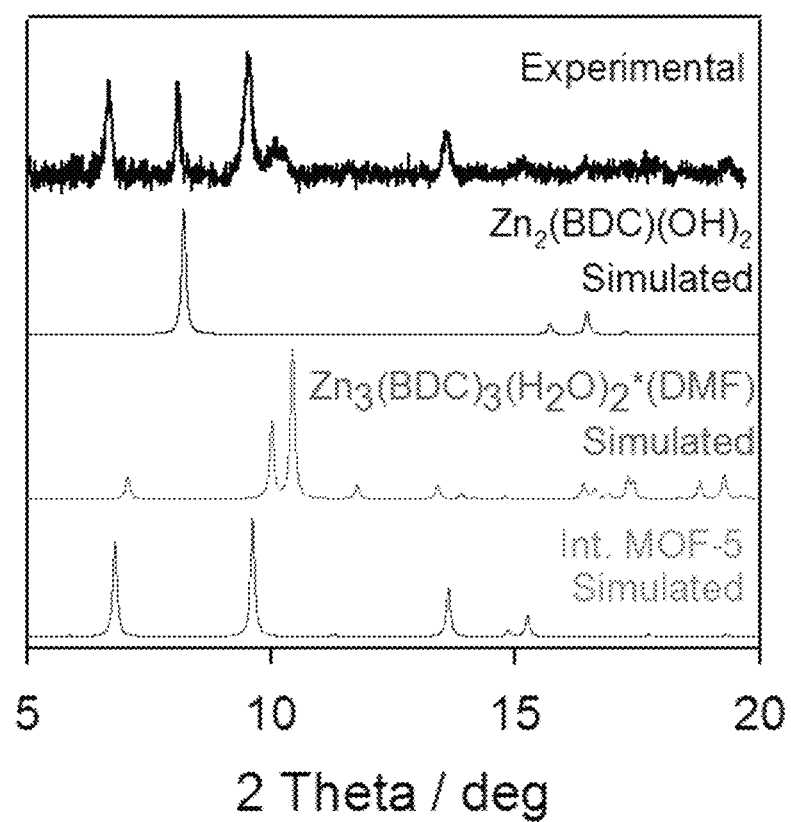
FIG. 10 is a graph of powder X-ray diffraction results for $Zn_2(BDC)(OH)_2$, $Zn_3(BDC)_3(H_2O)_2$*(DMF), and interpenetrated MOF-5 synthesized using cathodic electrodeposition, according to an illustrative embodiment of the invention.

Cathodic electrodeposition was used to synthesize Zn$_2$(BDC)(OH)$_2$, which exists as a minor co-precipitate in many reaction conditions. Attempts to store this metastable phase as a solid at ambient conditions were not successful. Also, due to lack of characteristic peaks after 20°, identification was solely based on the pattern's most intense peak at 8.22°. A sample procedure for synthesizing the metastable phase involved 85 mg of H$_2$BDC and 300 mg of Zn(NO$_3$)$_2$*6H$_2$O dissolved into a 10 mL solution of 0.1M TBAPF$_6$ in DMF (obtained from solvent column system, dried and deaeriated with argon). The cell, with a 1 cm$^2$ Pt mesh active electrode, a 4 cm$^2$ Pt mesh counter electrode, and a Ag/Ag (cryptand) reference electrode, was purged with 99.9% O$_2$ for 30 minutes and kept under O$_2$ atmosphere. After constant potential deposition at −1.5 V for 30 minutes, a light gray layer covered the active electrode. X-ray diffraction results and predictions for the material produced during the experiment are presented in FIG. 10.

Several of the above examples (e.g., synthesis of [Et$_3$NH]$_2$[Zn$_3$(BDC)$_4$]*DMF, Zn$_3$(BDC)$_3$(H$_2$O)$_2$*DMF, Zn(BDC)(H$_2$O)*DMF, Zn(BDC)(H$_2$O), and Zn$_2$(BDC)(OH)$_2$) may involve solid-state transformations from one to another, given different solvothermal environments. Other crystalline products could be identified as co-crystallizing with the described materials. Some of these exhibit powder X-ray diffraction (PXRD) peaks that match those of known structures, only when considering significant preferential orientation of the crystallites, as exemplified below.

Example 7

Figure 11:
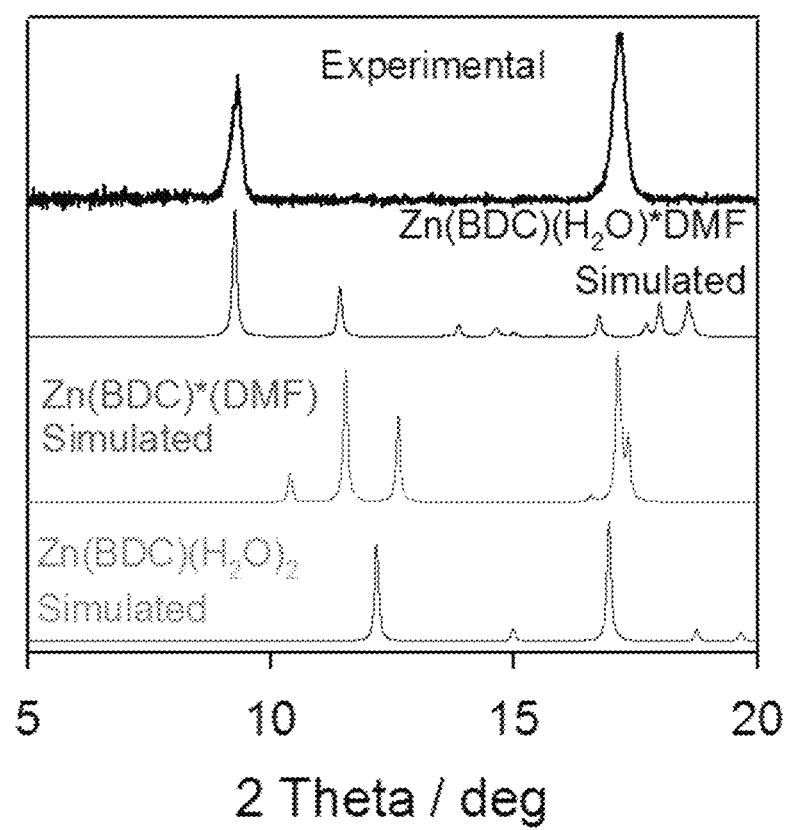
FIG. 11 is a graph of powder X-ray diffraction results for preferentially oriented $Zn_2(BDC)(OH)_2$ along with either preferentially oriented $Zn(BDC)*DMF$ or preferentially oriented $Zn(BDC)(H_2O)_2$ synthesized using cathodic electrodeposition, according to an illustrative embodiment of the invention.

The synthesis procedure of preferentially oriented Zn(BDC)(H$_2$O)*DMF and preferentially oriented Zn(BDC)*DMF or Zn(BDC)(H$_2$O)$_2$ began by dissolving 140 mg of anhydrous ZnCl$_2$, 170 mg of anhydrous NaNO$_3$, and 86 mg of H$_2$BDC in a 10 mL solution of 0.1 M TBAPF$_6$ in DMF (obtained from solvent column system, dried and deaeriated with argon). The solution was then transferred into a custom H-cell with a 1 cm$^2$ Pt mesh working electrode, a 4 cm$^2$ Pt mesh counter electrode, and a Ag/Ag (cryptand) reference electrode. The cell was then capped, stirred, and purged with compressed nitrogen at a pressure slightly above one atmosphere, until complete dissolution of solids had occurred. Under a N$_2$ blanket, electrolysis was performed in the quiescent solution at −1.50 V for 9 hours. X-ray diffraction results and predictions for the material produced during the experiment are presented in FIG. 11.

Example 8

In various embodiments, the cathodic electrodeposition methods described herein lead to the formation of new MOF phases. For example, in addition to controlled deposition of several phases in the Zn—BDC system, extension of the method to other metal ions has resulted in the discovery of new MOF phases that have not yet been accessed using traditional solvothermal conditions (i.e., heating in solvent). One such example, using Mn$^{2+}$ instead of Zn$^{2+}$, is shown below.

Cathodic electrodeposition was used to synthesize Mn(BDC)(H$_2$O)$_2$. The process began by stirring 85 mg of H$_2$BDC and 400 mg of Mn(NO$_3$)$_2$*4H$_2$O in a 10 mL solution of 0.1 M TBAPF$_6$ in DMF (obtained from solvent column system, dried and deaeriated with argon) solution under nitrogen purge for 30 minutes inside a custom H-cell, containing a 1 cm$^2$ Pt mesh working electrode, a 4 cm$^2$ Pt mesh counter electrode, and a Ag/Ag (cryptand) reference electrode. The cell was purged with N$_2$ and electrolyzed at −1.5 V for 24 hours under a N$_2$ atmosphere. A white solid layer formed on the electrode after deposition, which decomposed to a known structure in ambient conditions over 12 hours.

Figure 12:
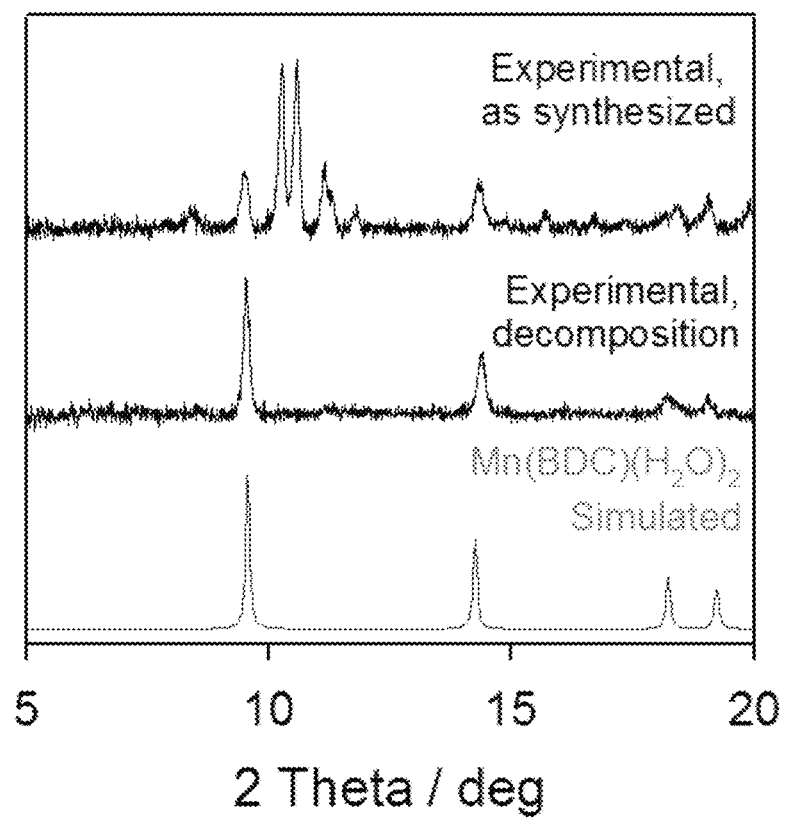
FIG. 12 is a graph of powder X-ray diffraction results for $Mn(BDC)(H_2O)_2$ synthesized using cathodic electrodeposition, according to an illustrative embodiment of the invention.

X-ray diffraction results and predictions for the material produced during the experiment are presented in FIG. 12. As shown, Mn(BDC)(H$_2$O)$_2$ has been produced. The material contains Mn(BDC)(H$_2$O)$_2$ and another metastable crystalline phase. The two strong peaks at 10-12 degrees 2 Theta in the top trace of the figure cannot be identified in known Mn—BDC or Zn—BDC and therefore represent a new Mn—BDC phase. This phase decomposed when left in the air to Mn(BDC)(H$_2$O)$_2$, as shown by the middle trace.

Example 9

In certain embodiments, the conductive surface or working electrode used to produce the MOFs by cathodic electrodeposition may include or consist of any conductive material. Many of the example procedures described herein utilized FTO or platinum as the conductive surface. The use of platinum was mainly due to its enhanced catalytic properties in nitrate-water reduction and its relative chemical inertness as a noble metal. Use of a platinum conductive surface may therefore reduce the required potential for electrodeposition and importantly eliminate Zn metal deposition, which accompanied MOF-5 deposition when using an FTO working electrode.

Figure 13:
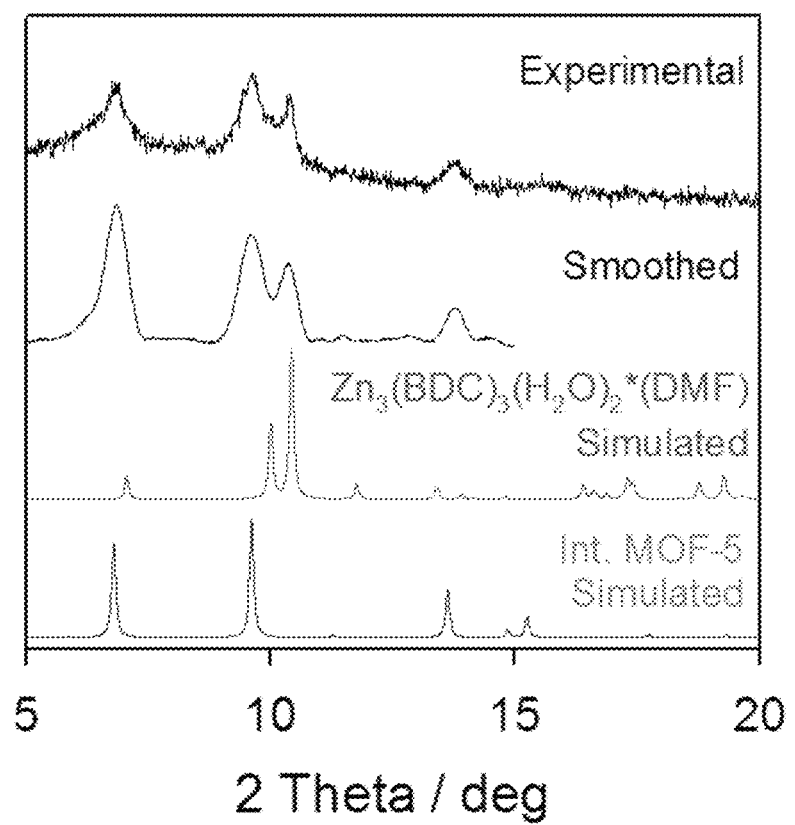
FIG. 13 is a graph of powder X-ray diffraction results for $Zn_3(BDC)_3(H_2O)_2*(DMF)$ and interpenetrated MOF-5 synthesized using cathodic electrodeposition on a copper surface, according to an illustrative embodiment of the invention.

Metallic copper was used as the conductive surface for the synthesis of interpenetrated MOF-5. The process began inside a glovebox filled with N$_2$, where 85 mg of H$_2$BDC and 250 mg of Zn(NO$_3$)$_2$*6H$_2$O were added to a two-compartment glass cell. The solids were dissolved in a 10 mL solution of 0.1 M TBAPF$_6$ in dry and deaerated DMF solution with 1% v/v water. The conductive surface or working electrode was a 1.5×1 cm$^2$ copper sheet (30 gauge, 99.95%), the auxiliary electrode was a 1 cm$^2$ Pt mesh, and the reference electrode was Ag/Ag (cryptand). Approximately 1×1 cm$^2$ of the copper sheet was submerged in solution. A constant potential of −1.25 V was applied for 60 minutes. X-ray diffraction results and predictions for the material produced during the experiment are presented in FIG. 13. Zn$_3$(BDC)$_3$(H$_2$O)$_2$*DMF co-precipitates in this reaction.

Example 10

In certain embodiments, nitrate reduction is used as the electrochemical basis for generating the base species necessary for ligand (e.g., H$_2$BDC) deprotonation. Nitrate may therefore serve as the probase (i.e., a stable molecule in solution that can be electrochemically reduced to form active base species for deprotonation of the ligand) in such methods.

In general, the methods described herein may utilize a wide variety of molecules (e.g., other than nitrate) as the probase. For example, in the synthesis of [Et$_3$NH]$_2$[Zn$_3$(BDC)$_4$]*DMF, described above, triethylammonium chloride was used as a probase (i.e., reduction of triethylammonium produces triethylamine). Also, as described above for the synthesis of Zn$_3$(BDC)$_3$(H$_2$O)$_2$*DMF, Zn(BDC)(H$_2$O)*DMF, and Zn(BDC)(H$_2$O), molecular oxygen was used as a probase (O$_2$ reduction in the presence of water produces hydroxide). In general, any molecular species or ion that becomes a proton acceptor upon reduction may be considered to be a probase (e.g., a Brønsted probase). Even when the probase exhibits reversible protonation, the cathodic potential at the electrode may allow a fraction of free ligands to exist. In some embodiments, the protonated ligands themselves function as probases. For example, reduction of H$_2$BDC with evolution of H$_2$ generates HBDC$^−$, which may itself participate in the deposition process.

Figure 14:
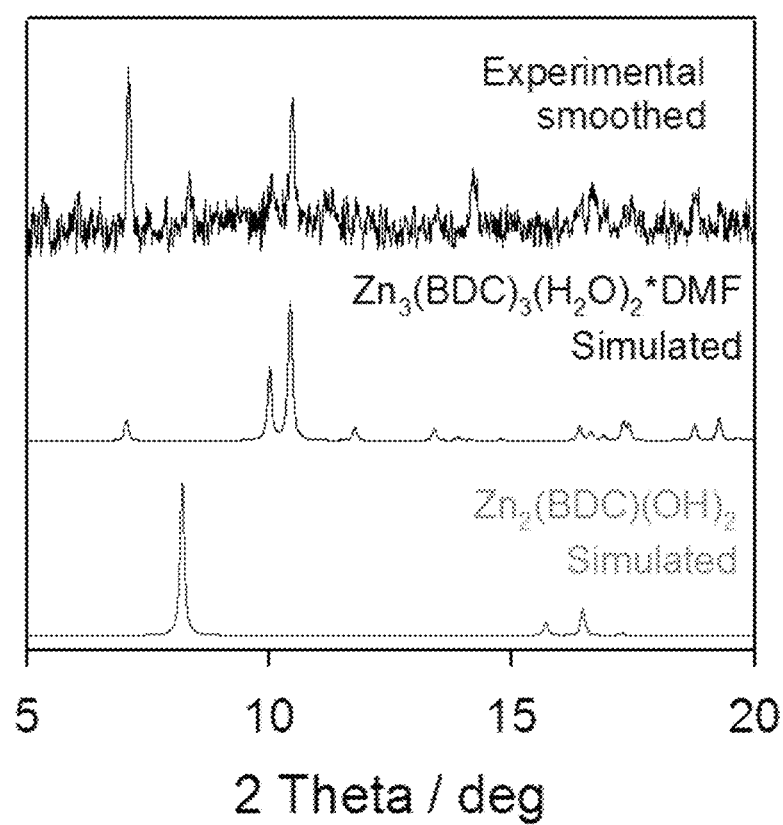
FIG. 14 is a graph of powder X-ray diffraction results for $Zn_3(BDC)_3(H_2O)_2*DMF$ and $Zn_2(BDC)(OH)_2$ synthesized using cathodic electrodeposition, according to an illustrative embodiment of the invention.

One experiment utilized used benzoquinone as a probase. The procedure began by dissolving 85 mg of H$_2$BDC, 300 mg of Zn(NO$_3$)$_2$*6H$_2$O, and 110 mg of benzoquinone in a 10 mL solution of 0.1 M TBAPF$_6$ in DMF (obtained from solvent column system, dried and deaeriated with argon) under nitrogen purge for 30 minutes inside a custom H-cell. The custom H-cell included a 1 cm$^2$ Pt mesh working electrode, a 4 cm$^2$ Pt mesh counter electrode, and a Ag/Ag (cryptand) reference electrode. The cell was electrolyzed at −0.85 V for 12 hrs. X-ray diffraction results and predictions for the Zn$_3$(BDC)$_3$(H$_2$O)$_2$*DMF material produced during the experiment are presented in FIG. 14.

EQUIVALENTS

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A method for preparing a crystalline metal-organic framework (MOF), the method comprising the steps of:
providing an electrolyte solution in contact with a conductive surface, the electrolyte solution comprising a protonated organic ligand, a metal ion, and a probase; and
applying a current or potential to the conductive surface in contact with the electrolyte solution, thereby producing the crystalline metal-organic framework (MOF) deposited on the conductive surface.

2. The method of claim 1, wherein the protonated organic ligand contains a proton with an acidity constant ($pK_a$ in water and at 25° C.) having a value from 0 to 15 such that the proton can be removed in situ by an electrochemically produced base species.

3. The method of claim 2, wherein the electrochemically produced base species is a hydroxide anion.

4. The method of claim 2, wherein the electrochemically produced base species is an amine.

5. The method of claim 1, wherein the organic ligand comprises one or more members selected from the group consisting of a carboxylic acid, a tetrazole, a 1,2,3-triazole, a 1,2,4-triazole, a pyrazole, a sulfonic acid, a phosphonic acid, a sulfinic acid, a phosphinic acid, and an imidazole.

6. The method of claim 1, wherein the metal ion comprises a member selected from the group consisting of $Zn^{2+}$, $Cu^{2+}$, $Cu^+$, $Co^{2+}$, $Co^{3+}$, $Ni^{2+}$, $Mn^{2+}$, $Mn^{3+}$, $Mn^{4+}$, $Fe^{2+}$, $Fe^{3+}$, $V^{2+}$, $V^{3+}$, $Cr^{2+}$, $Mo^{2+}$, $W^{2+}$, $Ru^{2+}$, $Os^{2+}$, $Cd^{2+}$, $Be^{2+}$, $Mg^{2+}$, $Ca^{2+}$, $Ba^{2+}$, $Sr^{2+}$, and $Ln^{3+}$ where Ln is any of the lanthanide ions.

7. The method of claim 1, wherein the conductive surface comprises one or more members selected from the group consisting of fluorine doped tin oxide (FTO), indium tin oxide (ITO), silicon, carbon, graphite, zinc, cobalt, nickel, copper, titanium, iron, and steel.

8. The method of claim 1, wherein the conductive surface catalyzes the reduction of the probase to generate a base species.

9. The method of claim 1, wherein the conductive surface is transparent or semi-transparent.

10. The method of claim 1, wherein the deposition of the crystalline metal-organic framework on the conductive surface is cathodic electrodeposition rather than anodic electrodeposition, such that the conductive surface does not undergo corrosion during the deposition.

11. The method of claim 1, wherein the current or potential is applied to the conductive surface in contact with the electrolyte solution such that the probase is reduced at or near the conductive surface, thereby generating a base species, wherein the protonated organic ligand is deprotonated in situ by reaction with the base species, and wherein the deprotonated organic ligand reacts with the metal ion, thereby producing the crystalline metal-organic framework deposited on the conductive surface.

12. The method of claim 1, wherein the probase comprises an oxoanion.

13. The method of claim 12, wherein the oxoanion comprises a member selected from the group consisting of nitrate ($NO_3^-$), perchlorate ($ClO_4^-$), and sulfate ($SO_4^{2-}$).

14. The method of claim 1, wherein the probase comprises a member selected from the group consisting of water, molecular oxygen ($O_2$), triethylammonium, benzoquinone, and a benzoquinone derivative.

15. The method of claim 1, wherein the probase comprises an ammonium cation.

16. The method of claim 1, wherein the deposition of the crystalline metal-organic framework on the conductive surface is performed in a single step.

17. The method of claim 1, wherein the deposition of the crystalline metal-organic framework on the conductive surface is performed at room temperature.

* * * * *